(12) United States Patent
Rehe

(10) Patent No.: US 9,398,839 B2
(45) Date of Patent: Jul. 26, 2016

(54) PROTECTIVE SLEEVE FOR AN ENDOSCOPE HAVING AN ENDOSCOPE TUBE

(71) Applicant: Henke-Sass, Wolf GmbH, Tuttlingen (DE)

(72) Inventor: Oliver Rehe, Tuttlingen (DE)

(73) Assignee: Henke-Sass, Wolf GmbH, Tuttlingen (DE)

( * ) Notice: Subject to any disclaimer, the term of this patent is extended or adjusted under 35 U.S.C. 154(b) by 295 days.

(21) Appl. No.: 13/855,892

(22) Filed: Apr. 3, 2013

(65) Prior Publication Data

US 2013/0267778 A1    Oct. 10, 2013

(30) Foreign Application Priority Data

Apr. 4, 2012 (DE) .......................... 10 2012 205 598

(51) Int. Cl.
*A61B 1/00* (2006.01)

(52) U.S. Cl.
CPC ......... *A61B 1/00142* (2013.01); *A61B 1/00096* (2013.01); *A61B 1/00135* (2013.01); *A61B 1/00179* (2013.01)

(58) Field of Classification Search
CPC ........... A61B 1/00096; A61B 1/00101; A61B 1/00181; A61B 1/00142

USPC .................................. 600/121, 122, 176, 186
See application file for complete search history.

(56) References Cited

U.S. PATENT DOCUMENTS

| | | | |
|---|---|---|---|
| 3,809,072 A | 5/1974 | Ersek et al. | |
| 3,856,000 A | 12/1974 | Chikama | |
| 4,140,364 A | 2/1979 | Yamashita et al. | |
| 5,693,043 A | 12/1997 | Kittrell et al. | |
| 6,413,209 B1 | 7/2002 | Thompson | |
| 8,414,480 B2* | 4/2013 | Kendale et al. | 600/175 |
| 2002/0128538 A1* | 9/2002 | Thompson | 600/121 |
| 2003/0092966 A1 | 5/2003 | Schara et al. | |
| 2004/0236183 A1 | 11/2004 | Durell | |
| 2008/0208006 A1 | 8/2008 | Farr | |
| 2009/0177094 A1 | 7/2009 | Brown et al. | |
| 2009/0306474 A1 | 12/2009 | Wilson | |
| 2010/0324372 A1 | 12/2010 | Buerk et al. | |
| 2011/0028790 A1 | 2/2011 | Farr et al. | |
| 2012/0136213 A1* | 5/2012 | Weimer et al. | 600/173 |
| 2012/0232408 A1 | 9/2012 | Weller-Brophy | |

\* cited by examiner

*Primary Examiner* — John P Leubecker
*Assistant Examiner* — Rajaa El Alami
(74) *Attorney, Agent, or Firm* — Skaar Ulbrich Macari, P.A.

(57) ABSTRACT

A protective sleeve for an endoscope having an endoscope tube is provided. The protective sleeve of certain embodiments can include a tubular main body for holding a distal section of the endoscope tube. The main body has an open proximal end and a cover glass at the distal end. The cover glass has a spherically curved, concave inside, a spherically curved, convex outside and a constant thickness.

14 Claims, 3 Drawing Sheets

PROTECTIVE SLEEVE FOR AN ENDOSCOPE HAVING AN ENDOSCOPE TUBE

PRIORITY

This application claims priority to German Patent Application No. 102012205598.3, filed on Apr. 4, 2012, which is hereby incorporated herein by reference in its entirety.

FIELD

The present invention relates to a protective sleeve for an endoscope having an endoscope tube.

BACKGROUND

Endoscopes are often used to visualize a surgical site. Mechanical damage to the endoscope can easily occur if there is undesired contact with a surgical instrument. In order to prevent this, a protective sleeve with a cover glass can be provided, with the result that only the protective sleeve, and not the endoscope, is damaged.

As the surgical site is often filled with a saline solution, there is refraction at the transition between the saline solution and the cover glass of the protective sleeve, which leads to deterioration of the imaging properties of the endoscope. In particular, e.g. the maximum angle of view of the imaging lens system can be reduced.

SUMMARY

Starting from this, the object of the invention is therefore to provide an improved protective sleeve for an endoscope having an endoscope tube.

According to certain embodiments of the invention, the object is achieved by a protective sleeve for an endoscope having an endoscope tube, wherein the protective sleeve comprises a tubular main body for receiving a distal section of the endoscope tube, the main body has an open proximal end and a cover glass at the distal end and wherein the cover glass has a spherically curved, concave inside, a spherically curved, convex outside and a constant thickness.

The light beams coming from every object point and used for the image generation thereby advantageously pass through the cover glass perpendicularly or substantially perpendicularly, with the result that the cover glass brings about no or only a very small refraction. As a result, the influence of the medium on the outside of the cover glass is practically negligible, with the result that e.g. the angle of view of an endoscope with fitted protective sleeve stays practically the same in air and in a saline solution. The protective sleeve according to the invention thus on the one hand protects the endoscope and on the other hand leads to no deterioration of the optical imaging properties of the imaging lens system of the endoscope if the endoscope with fitted protective sleeve is used in a liquid medium.

In the protective sleeve according to certain embodiments of the invention, the centres of the radii of curvature of the inside and outside can coincide.

The tubular main body of the protective sleeve can be formed from (e.g. transparent) plastic. In the same way, the cover glass can be formed from plastic. A very cost-effective protective sleeve can thereby be provided. The protective sleeve can be formed for example as a deep-drawn part, with the result that the protective sleeve can be provided as a disposable part.

The distal end of the main body of the protective sleeve according to certain embodiments of the invention is sealed. Thus, e.g. the endoscope tube inserted into the protective sleeve can be protected against an aqueous medium in which the protective sleeve, together with inserted endoscope tube, is immersed.

In the protective sleeve according to certain embodiments of the invention, the main body can include, at the proximal end, a first locking element which, in conjunction with a second locking element on the endoscope, enables a releasable locking of the protective sleeve when the endoscope tube is inserted. In particular, the second locking element can be provided on the endoscope tube itself. The two locking elements can be designed e.g. such that a bayonet lock is implemented. However, any other type of releasable connection or locking is also possible.

In the protective sleeve according to certain embodiments of the invention, the inside and/or the outside of the cover glass can be antireflection-coated.

The protective sleeve according to certain embodiments of the invention can include, at the distal end of the main body, a transparent area spaced apart from the cover glass for illumination light of the endoscope, wherein the transparent area has a spherically curved, concave inside, a spherically curved, convex outside and a constant thickness, at least in one direction. In particular, the transparent area can include a spherically curved, concave inside, a spherically curved, convex outside and a constant thickness in two orthogonal directions.

The area between the cover glass and the transparent area at the distal end can in particular be formed as a non-transparent area. It can e.g. be blackened. Naturally, the whole area at the distal end next to the cover glass and next to the transparent area can also be formed as a non-transparent area (for example blackened).

The main body of the protective sleeve according to certain embodiments of the invention is preferably formed rigid. Also, the endoscope tube is preferably formed rigid.

Furthermore, an endoscope with an endoscope tube, an imaging lens system arranged in the endoscope tube and a protective sleeve according to certain embodiments of the invention (including its described developments) is provided, wherein a distal section of the endoscope tube is inserted into the protective sleeve, the protective sleeve is releasably attached to the endoscope and the imaging lens system projects an image of an object located in front of the cover glass. Such a combination of endoscope and protective sleeve ensures that the endoscope has good imaging properties in an aqueous medium and that the endoscope tube is protected against the aqueous medium as well as against mechanical damage.

In the endoscope according to certain embodiments of the invention, the centres of the radii of curvature of the inside and outside of the cover glass can coincide and lie in the entrance pupil of the imaging lens system. Very good imaging properties are thus achieved. In particular, the influence on the imaging onto the cover glass is minimized.

In the endoscope according to certain embodiments of the invention, the imaging lens system can include a swivellably mounted deflecting element with which the viewing direction through the cover glass can be set. The deflecting element can include a surface that brings about the beam deflection. The centres of the radii of curvature of the inside and outside of the cover glass can preferably coincide and lie on the swivel axis of the deflecting element or in the surface that brings about the beam deflection.

In addition, the imaging lens system can include several lenses, wherein the lens of the imaging lens system positioned closest to the cover glass is formed as a plano-convex lens the flat side of which faces the cover glass.

It is understood that the features mentioned above and those yet to be explained below can be used, not only in the stated combinations, but also in other combinations or alone, without departing from the scope of the present invention.

BRIEF DESCRIPTION OF THE DRAWINGS

The invention is explained in further detail below by way of example with reference to the attached drawings which also disclose features essential to the invention. There are shown in.

DETAILED DESCRIPTION

The present invention can be explained with reference to the following example embodiments. However, these example embodiments are not intended to limit the present invention to any specific examples, embodiments, environments, applications or implementations described in these embodiments. Therefore, description of these embodiments is only for purpose of illustration rather than to limit the present invention.

Figure 1:
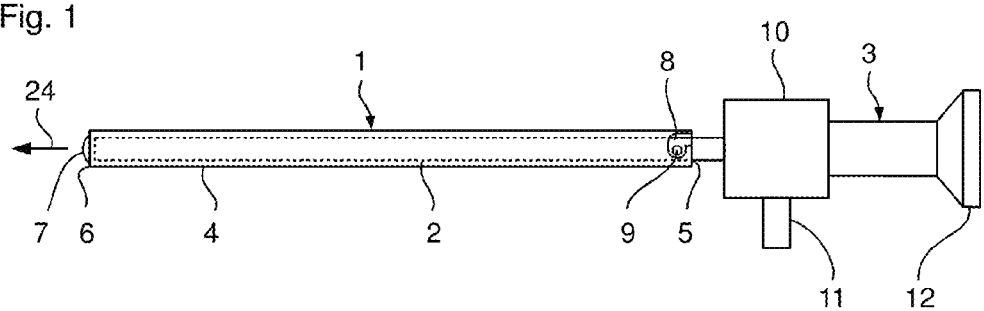
FIG. 1 is a schematic representation of the protective sleeve according to an embodiment of the invention, pushed onto an endoscope tube of an endoscope.
Figure 2:
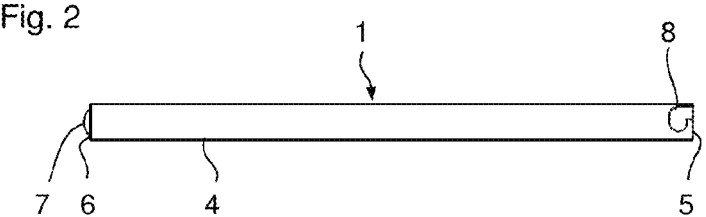
FIG. 2 is a schematic representation of the protective sleeve of FIG. 1.
Figure 3:
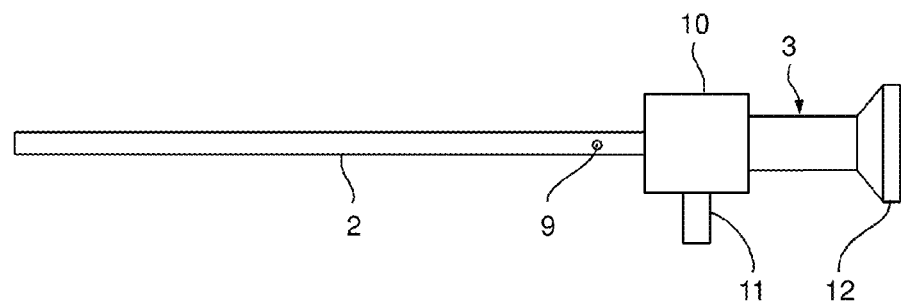
FIG. 3 is a schematic representation of the endoscope of FIG. 1.

In the embodiment shown in FIG. 1, the protective sleeve 1 according to an embodiment of the invention is pushed onto the endoscope tube 2 of an endoscope 3, which can be formed in particular as an arthroscope. The protective sleeve 1 is shown alone in FIG. 2 and the endoscope 3 without protective sleeve 1 is shown in FIG. 3.

The protective sleeve 1 has a tubular main body 4 which comprises an open proximal end 5 and a distal end 6, wherein the distal end 6 is sealed by means of a cover glass 7. At the proximal end 5 of the main body 4, a recess 8 is formed which is shaped such that, together with a pin 9 attached to the endoscope tube 2, it enables a releasable connection between protective sleeve 1 and endoscope tube 2 in the manner of a bayonet connection.

In addition to the endoscope tube 2, the endoscope 3 has a main part 10 which is connected to the proximal end of the endoscope tube 2. The endoscope 2 can comprise an illumination unit for illuminating the object to be imaged. In the present embodiment, the illumination unit comprises a connector 11 formed on the main part 10, via which illumination light can be coupled into the endoscope 3. For example, optical fibres, via which the light for illuminating an object to be imaged is transmitted, can run from the connector 11 to the distal end of the endoscope tube 2. Naturally, the connector can also be omitted if the desired illumination light is provided in another manner when the endoscope is being used.

Furthermore, an eyepiece 12 is also connected to the main part 10. Instead of the eyepiece 12 or in addition to the eyepiece 12, a connector for a camera can be formed on the main part 10.

In the endoscope tube 2, an imaging lens system is arranged which projects an image of an object located in front of the cover glass 7 (when the endoscope tube 2 is inserted into the protective sleeve 1 in the manner shown in FIG. 1). The object imaged in this way can then be transmitted to the eyepiece 12 e.g. in known manner through rod lenses arranged in the endoscope tube 2.

Figure 4:
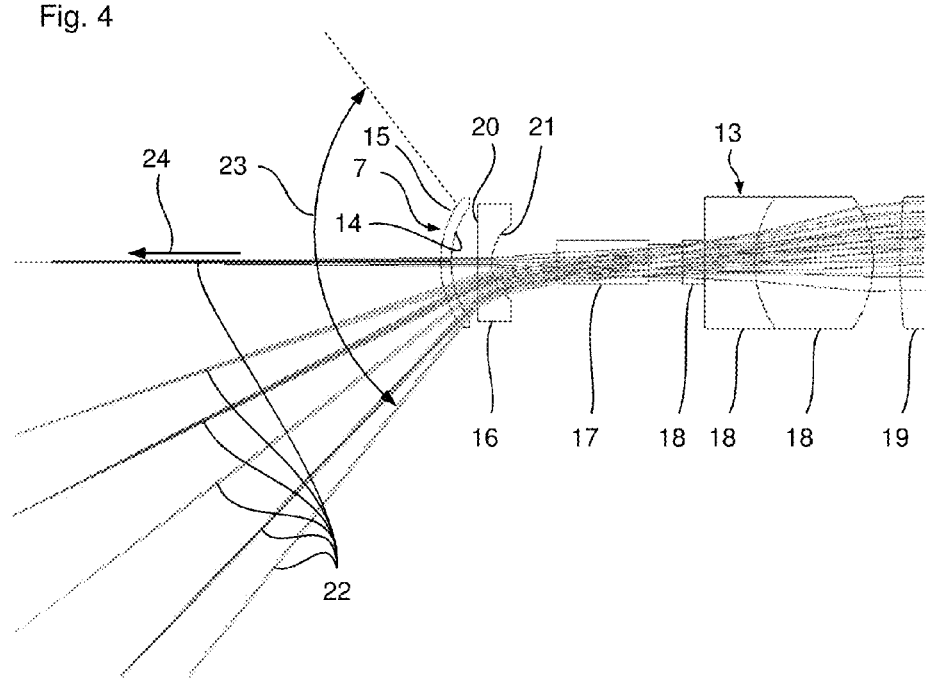
FIG. 4 is a schematic representation of the cover glass of the protective sleeve according to an embodiment of the invention and of the imaging lens system in the distal end area of the endoscope tube.

The elements of the imaging lens system 13 in the area of the distal end of the endoscope tube 2 and also the cover glass 7 of the protective sleeve 1 are represented schematically in FIG. 4.

The cover glass 7 has a spherically curved, concave inside 14 and a spherically curved, convex outside 15, wherein the centres of curvature of inside and outside 14, 15 coincide. Thus, the thickness of the cover glass 7 is constant. In the embodiment described here, the thickness of the cover glass lies in the range of 0.1-0.3 mm. It can be e.g. 0.2 mm. The cover glass 7 can therefore also be called a domed glass.

The imaging lens system 13 has a distal lens 16, a prism 17 that can optionally be provided, lenses 18 and a field lens 19.

The distal lens 16 is formed as a plano-concave lens, wherein its flat side 20 faces the cover glass 7 and its concave side 21 faces away from the cover glass 7. The distal lens 16 is formed as a negative lens.

Light bundles 22 are drawn in to illustrate the imaging properties of the imaging lens system 13. In order to simplify the representation, however, the light bundles 22 are only shown for half the angle of view 23.

The described configuration of the cover glass 7 achieves the advantage that the beams originating from each object point and used for the image generation (in particular the main beams of each light bundle) pass through the cover glass 7 perpendicularly or substantially perpendicularly. The cover glass 7 can therefore be seen as an element that is substantially neutral for the imaging (which has essentially no optical imaging properties), with the result that the cover glass 7 can also be called a null lens. As the beams used for the image generation pass through the cover glass 7 perpendicularly or substantially perpendicular, advantageously no or an essentially negligible refraction occurs irrespective of the medium present on the outside 15 of the cover glass 7.

Thus, e.g. in the arthroscopy of knees and shoulder joints, in most cases the surgical site is filled with a saline solution. An endoscope is used to visualize the area to be operated on. The large angle of view of e.g. 105°, as shown in FIG. 4, can be maintained, or at least almost maintained, by the protective sleeve 1 according to the invention with the cover glass 7 and a reduction of the angle of view to e.g. 75° no longer occurs as is the case if the endoscope has e.g. a flat cover glass.

In the embodiment described in conjunction with FIGS. 1 to 4, the viewing direction 24 of the endoscope 2 is parallel to the longitudinal direction of the endoscope tube 2. A viewing direction of 0° is also referred to here.

Figure 5:
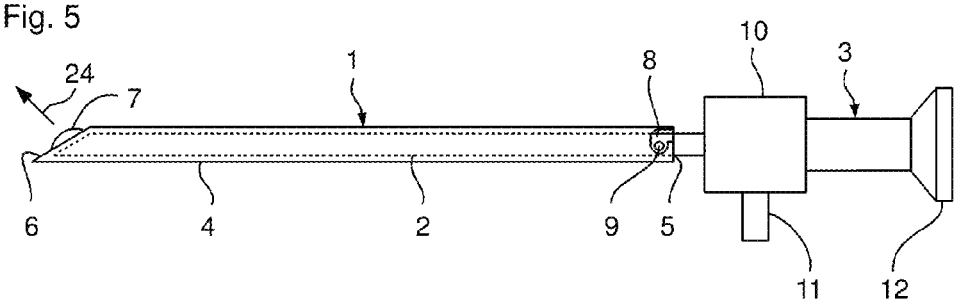
FIG. 5 is a further embodiment of the protective sleeve according to an embodiment of the invention, pushed onto an endoscope tube of an endoscope.
Figure 6:
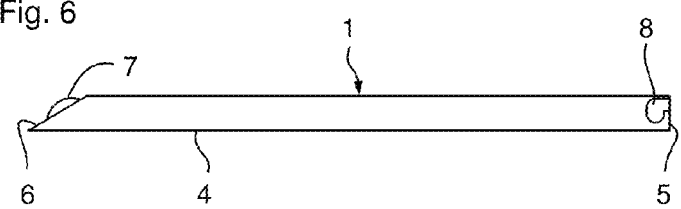
FIG. 6 is the protective sleeve according to an embodiment of the invention according to FIG. 5.
Figure 7:
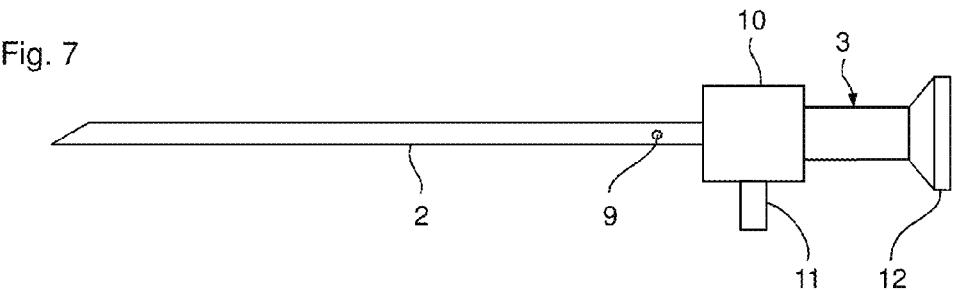
FIG. 7 is the endoscope according to FIG. 5.

In FIGS. 5 to 7, modifications of the protective sleeve 1 according to the invention are shown, for an endoscope 3 with a viewing direction 24 of approx. 45°. In this case, the protective sleeve 1 is adapted accordingly at the distal end 6. In any case, a cover glass 7 with constant thickness and spherically curved, concave inside 14 as well as spherically curved, convex outside 15 is again provided. With such a viewing direction, a beam deflection between cover glass 7 on the one hand and the further lens system in the endoscope tube 2 on the other hand is necessary for folding the beam path. The prism 17 mentioned in connection with FIG. 4 can be provided for this. In this case, the distal lens 16 is positioned between cover glass 7 and prism 17 (when the protective sleeve 1 is pushed on). Naturally, the distal lens 16 can also be positioned behind the prism 17.

In addition to the described optical advantages, the protective sleeve 1 according to the invention also has the purpose of protecting the distal end of the endoscope tube 2. In particular, the distal end of the endoscope tube 2 is to be protected against mechanical damage which can easily occur during the use according to the invention of the endoscope 3 (e.g. in the arthroscopy of knee and shoulder joints). If e.g. contact with a surgical instrument occurs, only the protective sleeve 1 is damaged and the more valuable endoscope 3 remains unharmed.

It is therefore of particular advantage if the protective sleeve 1 is designed as a cost-effective disposable part. In particular, the protective sleeve 1 can be produced entirely from plastic.

Figure 8:
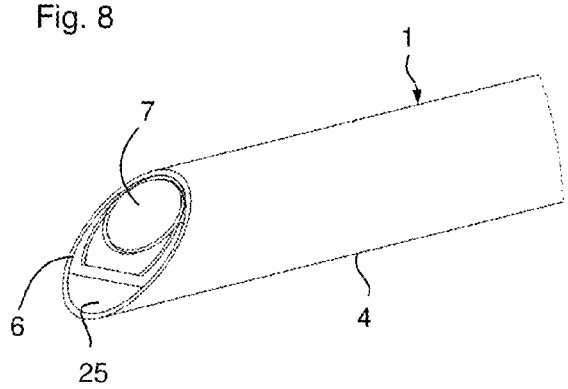
FIG. 8 is a perspective representation of the distal end section of the protective sleeve according to an embodiment of the invention according to FIGS. 5 and 6.

The distal end area of the protective sleeve 1 according to FIGS. 5 and 6 is shown in perspective in FIG. 8. In addition to the cover glass 7, the protective sleeve 1 can also have, at its distal end 6, a second transparent area 25 through which the light for illumination passes from the endoscope tube 2 towards the object to be imaged.

Figure 9:
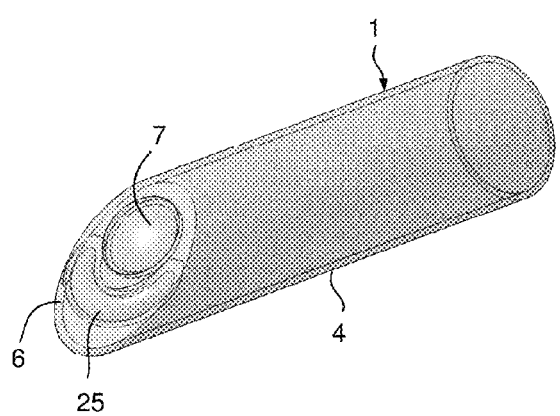
FIG. 9 is a perspective representation of the distal end section of a further embodiment of the protective sleeve according to the invention.

As shown in the perspective representation of the distal end area of a further embodiment of the protective sleeve according to the invention in FIG. 9, this transparent area 25 can also be formed such that it has a spherically curved, concave inside and a spherically curved, convex outside with constant thickness, at least in one direction. The illumination unit can be configured such that the light for illumination can pass through the transparent area 25 perpendicularly or substantially perpendicular, so that no or an essentially negligible refraction occurs irrespective of the medium present on the outside of the transparent area 25. The transparent area 25 can therefore also be called a null ring or partial null ring. Here, the transparent area 25 is adapted to the shape of the light emission at the distal end of the endoscope tube 2 and has a semi-circular shape in top view.

The cover glass 7 and optionally the transparent area 25 can be designed e.g. as a deep-drawn part. In particular, the whole protective sleeve 1 can be designed as a deep-drawn part. Furthermore, the distal end 6 of the tubular main body 4 next to the cover glass 7 and optionally next to the transparent area 25 can be blackened in order to minimize undesired reflexes. In addition, the inside and/or outside 14, 15 of the cover glass 7 can be provided with an anti-reflective coating.

The cover glass 7 is preferably designed such that the centres of the two radii of curvature of inside and outside 14, 15 coincide with the position of the entrance pupil of the imaging lens system 13 when the protective sleeve 1 is connected to the endoscope 3 in the designated manner, as shown in FIGS. 1 and 5. The position of the entrance pupil is determined by the intersection points of the main beams (central light beam of the light bundles 22) and is ideally one point. Due to the presence of pupil aberrations in the actual system, the entrance pupil is most often slightly curved and therefore cannot be found precisely at one point. In this case, the centres of the curvatures of inside and outside 14 and 15 can lie e.g. in the centre of the various intersection points.

In the embodiments shown in FIGS. 8 and 9, the tubular main body 4 can in each case be formed transparent.

Naturally, the protective sleeve 1 according to the invention can also be provided for endoscopes with variable viewing direction. In these endoscopes, the imaging lens system 13 has a swivellable deflecting element with which the viewing direction can be adjusted.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A protective sleeve for an endoscope having an endoscope tube, the protective sleeve comprising:
    a tubular main body holding a distal section of the endoscope tube, wherein the main body has an open proximal end and a cover glass at the distal end, and wherein the cover glass has a spherically curved, concave inside, a spherically curved, convex outside and a constant thickness,
    wherein a transparent area, spaced apart from the cover glass, for illumination light of the endoscope is defined at the distal end of the main body, wherein the transparent area includes a spherically curved, concave inside, a spherically curved, convex outside and a constant thickness, at least in one direction, and
    wherein the area between the cover glass and the transparent area at the distal end is formed as a non-transparent area.

2. The protective sleeve according to claim 1, wherein the centers of the radii of curvature of the inside and outside of the cover glass coincide.

3. The protective sleeve according to claim 1, wherein the tubular main body is formed from plastic.

4. The protective sleeve according to claim 1, wherein the cover glass is formed from plastic.

5. The protective sleeve according to claim 1, wherein the distal end of the main body is sealed.

6. The protective sleeve according to claim 1, wherein the main body includes, at the proximal end, a first locking element which, in conjunction with a second locking element on the endoscope, provides a releasable locking of the protective sleeve when the endoscope tube is inserted.

7. The protective sleeve according to claim 1, wherein at least one of the inside and the outside of the cover glass is antireflection-coated.

8. An endoscope, comprising:
    an endoscope tube;
    an imaging lens system arranged in the endoscope tube; and
    a protective sleeve according to claim 1,
    wherein a distal section of the endoscope tube is inserted into the protective sleeve, the protective sleeve is releasably attached to the endoscope and the imaging lens system is configured to project an image of an object located in front of the cover glass.

9. The endoscope according to claim 8, wherein the centers of the radii of curvature of the inside and outside of the cover glass coincide and lie in the entrance pupil of the imaging lens system.

10. The endoscope according to claim 8, wherein the imaging lens system includes a swivellably mounted deflecting element with which the viewing direction through the cover glass can be adjusted.

11. The endoscope according to claim 10, wherein the centers of the radii of curvature of the inside and outside of the cover glass coincide and lie on the swivel axis of the deflecting element.

12. The endoscope according to claim 11, wherein the deflecting element includes a surface that brings about a beam deflection, and wherein the centers of the radii of curvature of the inside and outside of the cover glass coincide and lie in the surface that brings about the beam deflection.

13. The endoscope according to claim 10, wherein the deflecting element includes a surface that brings about a beam deflection, and wherein the centers of the radii of curvature of the inside and outside of the cover glass coincide and lie in the surface that brings about the beam deflection.

14. The endoscope according to claim 8, wherein the imaging lens system includes several lenses, wherein the lens of the imaging lens system positioned closest to the cover glass is formed as a plano-convex lens the flat side of which faces the cover glass.

\* \* \* \* \*